(12) United States Patent
Traneus

(10) Patent No.: US 12,337,195 B2
(45) Date of Patent: Jun. 24, 2025

(54) RIPPLE FILTER UNIT FOR USE IN RADIOTHERAPY TREATMENT, METHODS FOR RADIOTHERAPY TREATMENT PLANNING AND DELIVERY AND COMPUTER PROGRAM PRODUCTS

(71) Applicant: RaySearch Laboratories AB, Stockholm (SE)

(72) Inventor: Erik Traneus, Uppsala (SE)

(73) Assignee: RaySearch Laboratories AB, Stockholm (SE)

( * ) Notice: Subject to any disclaimer, the term of this patent is extended or adjusted under 35 U.S.C. 154(b) by 891 days.

(21) Appl. No.: 15/734,031

(22) PCT Filed: Jul. 4, 2019

(86) PCT No.: PCT/EP2019/068029
§ 371 (c)(1),
(2) Date: Dec. 1, 2020

(87) PCT Pub. No.: WO2020/011650
PCT Pub. Date: Jan. 16, 2020

(65) Prior Publication Data
US 2021/0213302 A1    Jul. 15, 2021

(30) Foreign Application Priority Data

Jul. 12, 2018 (EP) .................................. 18183065

(51) Int. Cl.
*A61N 5/10*     (2006.01)
*G21K 1/10*    (2006.01)

(52) U.S. Cl.
CPC ............. *A61N 5/1031* (2013.01); *G21K 1/10* (2013.01); *A61N 2005/1087* (2013.01); *A61N 2005/1095* (2013.01)

(58) Field of Classification Search
CPC .......... A61N 5/1031; A61N 2005/1087; A61N 2005/1095; A61N 5/1043; G21K 1/10
See application file for complete search history.

(56) References Cited

U.S. PATENT DOCUMENTS

| 2003/0160189 A1 | 8/2003 | Matsuda | |
| 2009/0242789 A1 | 10/2009 | Tachikawa | |
| 2010/0264327 A1* | 10/2010 | Bonig | G21K 1/10 250/396 R |
| 2010/0327188 A1* | 12/2010 | Bert | A61N 5/10 250/492.3 |

(Continued)

FOREIGN PATENT DOCUMENTS

| EP | 2 241 350 A1 | 10/2010 |
| JP | H10-127792 A | 5/1998 |

(Continued)

*Primary Examiner* — David E Smith
*Assistant Examiner* — Christopher J Gassen
(74) *Attorney, Agent, or Firm* — Faegre Drinker Biddle & Reath LLP

(57) ABSTRACT

A ripple filter unit comprises a first and a second ripple filter, substantially identical, are arranged so that they overlap each other in a beam, with substantially the same orientation and movable relative to each other in such a way as to vary the filter characteristics dynamically. In this way, the modulation characteristics of the ripple filter unit can be varied.

13 Claims, 4 Drawing Sheets

(56) References Cited

U.S. PATENT DOCUMENTS

2011/0240874 A1\* 10/2011 Iwata ................... G21K 1/043
250/492.3

FOREIGN PATENT DOCUMENTS

| JP | H11-000408 A | 1/1999 | | |
|---|---|---|---|---|
| JP | 2002-191709 A | 7/2002 | | |
| JP | 6184313 B2 | 8/2017 | | |
| WO | WO-2014132481 A1 \* | 9/2014 | ........... | A61N 5/1077 |

\* cited by examiner

RIPPLE FILTER UNIT FOR USE IN RADIOTHERAPY TREATMENT, METHODS FOR RADIOTHERAPY TREATMENT PLANNING AND DELIVERY AND COMPUTER PROGRAM PRODUCTS

This application is the National Stage of International Application No. PCT/EP2019/068029, filed Jul. 4, 2019, and claims benefit of European Patent Application No. 18183065.4, filed Jul. 12, 2018, the entire contents of which are incorporated by reference herein.

TECHNICAL FIELD

The present invention relates to a ripple filter unit for use in radiotherapy treatment according to the preamble of claim 1 and a method for radiotherapy treatment planning using such a ripple filter unit, as well as to computer program products and apparatuses for radiotherapy treatment planning and delivery.

BACKGROUND

In pencil beam scanning, beams of charged particles, such as protons, are directed consecutively towards a number of spots within the patient, the spots covering the volume that is to be treated. The particles will deposit their energy along their path in the patient.

Each particle will deposit most of its energy towards the end of its path, in what is known as the Bragg peak. The depth of the Bragg peak's position within the patient depends on the initial energy of the particle. To cover a desired volume in a patient, different energy layers are defined such that particles of a particular energy layer will deposit their energy at a certain depth in the patient. The energy layers are selected in such a way that the Bragg peaks will be distributed over the volume to be treated.

The Bragg peaks of the different energy layers must overlap at a certain level to achieve a sufficient dose uniformity across the whole volume. The number of energy layers must therefore be high enough to avoid too great spacing of the Bragg peaks in the beam direction. At the same time, there is a desire to limit the number of energy layers, because changing from one energy layer to another takes time, thus making treatment times longer. Typically, changing energy layers can take approximately two seconds.

It has been proposed to make each Bragg peak wider by introducing a ripple filter in the beam. A ripple filter is a slab with a pattern of finely spaced ridges and valleys. The spatial separation between the ridges and valleys is small compared to the proton's lateral spread and the filter therefore effectively causes a broadening of the Bragg peaks. A common spacing is 1-6 mm. This means that each energy layer will cover a greater depth range in the patient, so that the number of energy layers can be reduced. Bragg peaks are narrower for energy layers with lower energy. This means that the positive effects of broadening the Bragg peak will be greater for the lower energy layers. During treatment delivery, a clinic typically uses one or two different ripple filters depending on the proximal-distal range to be covered. One ripple filter is inserted into the beam, usually manually. It may be kept throughout the treatment, or manually inserted or changed to another ripple filter between energy layers, which takes time.

EP2241350 discloses such a ripple filter, for expanding the particle energy distribution of a particle beam, proposing to create ripple filter arrangement comprising two ripple filters removably arranged in series in the radiation direction, and arranged at an angle of 90° relative to each other. This enables four discrete alternatives for modification of the energy distribution by inserting one or the other of the filters, none of them, or both.

SUMMARY

It is an object of the present invention to minimize the delivery time for radiotherapy treatment while maintaining plan quality.

The invention proposes a ripple filter unit for expanding the particle energy distribution of a particle beam, comprising a first and a second ripple filter, arranged in series in the beam path, substantially with the same orientation. The first and the second ripple filter are movable relative to each other in such a way as to vary the filter characteristics of the ripple filter unit dynamically by means of the relative positions of the first and the second ripple filter. Each of the first and second ripple filter will affect the beam as it traverses them, and the particles of the beam will be affected in different ways so that they will lose different amounts of energy depending on the relative position of the ripple filters. In particular, the particles' energy will be reduced by different amounts, depending on where they hit the ripple filter unit. For some relative positions the particles will be affected in substantially the same way in all positions on the ripple filter unit, which means the Bragg peak will not be broadened. For other relative positions the particles will be affected in different ways, so that they will lose different amounts of energy, which will lead to a broadening of the Bragg peak.

The ripple filter unit according to the invention is dynamic and can be adapted for each energy layer to achieve the optimal broadening of the Bragg peaks per energy layer. This allows the Bragg peak width to be varied without having to insert or exchange ripple filters during treatment. Typically, the ripple filter unit should be set to give less broadening for higher energy layers and to increase broadening for lower energy layers. By adjusting the ripple filter unit dynamically during treatment, the number of energy layers can be reduced without causing delays that would result, for example by using static ripple filters and changing them manually between energy layers. Preferably, the ripple filter unit is arranged to enable continuous movement of the first and second ripple filter relative to each other to enable smooth adjustment of the filter characteristics.

In a preferred embodiment, each of the first and the second ripple filter comprises a pattern of ridges and valleys and the first and second ripple filter are moveable relative to each other in such a way as to displace the ridges of the first and the second ripple filter relative to each other in a direction perpendicular to the ridges.

The movement is preferably a translational movement. One of the first and the second ripple filter may be fixed and the ripple filter that is not fixed may be translated relative to the ripple filter that is fixed. Alternatively, both ripple filters may be translated, preferably in opposite directions.

The first and the second ripple filter are preferably of the same type. In a preferred embodiment each filter is composed of uniform ridges positioned adjacent each other, the corners of the base of each ridge substantially touching adjacent ridges on each side of the ridge, except at the edges of the filter.

The ripple filter unit may be controlled to modulate the width of the Bragg peaks per energy layer or per individual spot. In the latter case, there may be more than one ripple filter setting for each energy layer.

The invention also relates to a method of generating a radiotherapy treatment plan where a ripple filter unit according to the above is used in dose delivery, comprising the steps of
- determining device parameters including ripple filter settings specifying a Bragg peak modulation
- generating the plan including said ripple filter settings.

The invention also relates to computer program products comprising computer readable code means, preferably stored on a non-transitory storage medium, which, when run in a processor will cause the processor to perform the treatment planning method as defined above.

The invention also relates to a computer system comprising a processor, a data memory and a program memory, wherein the program memory comprises a computer program product for the treatment planning method arranged to be run in the processor to control radiotherapy treatment planning.

The invention also proposes a treatment planning method and a treatment delivery method involving the optimization of such a ripple filter unit, computer program products for performing the methods and a computer system for performing the treatment planning method and a treatment delivery apparatus for delivering radiotherapy treatment to a patient according to the treatment delivery method.

The invention also proposes a method of delivering a pencil beam scan radiotherapy treatment to a patient, characterized in applying a ripple filter unit according to any one of the preceding claims in the beam and controlling the ripple filter unit to modulate the width of the Bragg peaks of the spots in an energy layer or between individual spots in an energy layer.

The invention also relates to a radiotherapy treatment apparatus comprising a processor for controlling radiotherapy treatment and a program memory comprising a dose delivery computer program product, arranged to be run in the processor to control the radiotherapy treatment apparatus.

BRIEF DESCRIPTION OF THE DRAWINGS

The invention will be described in more detail in the following, by way of example and with reference to the appended drawings, in which.

DETAILED DESCRIPTION

Figure 1A:
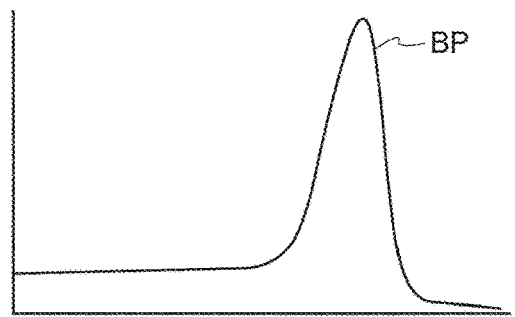
FIGS. 1a, 1b, and 1c show schematically a Bragg peak, a ripple filter according to the prior art and the resulting, wider Bragg peak when the ripple filter is arranged in the beam, respectively.

FIG. 1a shows the deposition of energy along a trajectory of a particle through a patient. As can be seen, most of the energy is deposited in a peak, denoted BP, near the end of the trajectory, known as the Bragg peak. The position and width of the Bragg peak depend on the initial energy of the particle.

Figure 1B:
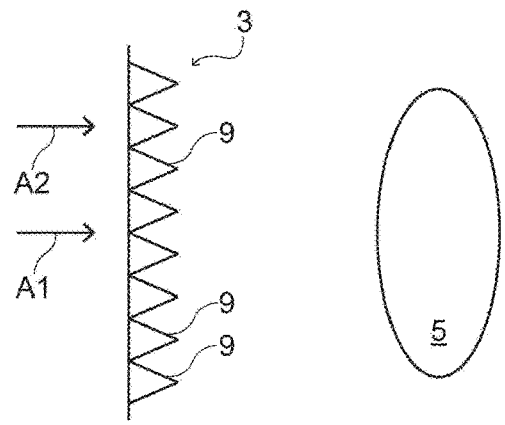

FIG. 1b shows a prior art ripple filter 3. The ripple filter 3 comprises a number of ridges 9, typically but not necessarily triangular in cross-section, positioned with their bases in one plane, their bases touching or nearly touching the bases of adjacent ridges. Preferably, all ridges are uniform. For clarity, only some of the ridges have reference signs. It is assumed that all particles passing through the filter towards a patient in a given period of time belong to the same energy layer so that their Bragg peaks should be at approximately the same depth. In the situation of FIG. 1b, however, a first particle, illustrated by a first arrow A1, will pass through the filter between two ridges and will ideally not lose any energy by passing the filter. In reality, of course, there will be a small energy loss. A second particle, illustrated by a second arrow A2, will pass through the filter near the peak of a ridge and will lose an amount of energy close to the maximum amount of energy that can be lost in the filter 3.

As will be understood, particles having the same initial energy and passing through the filter at different positions relative to the ridges 9 will lose different amounts of energy and will therefore reach different depths in the patients. This means that the Bragg peak for the energy layer will be broadened. It also means that some of the energy of the particles will be lost in the filter instead of being deposited in the patient. The ridges are not necessarily triangular, although this has been found to be a suitable shape. Also, they are not necessarily placed so that the valleys are triangular, although it is preferable that the ridges form a substantially continuous pattern on the filter.

Figure 1C:
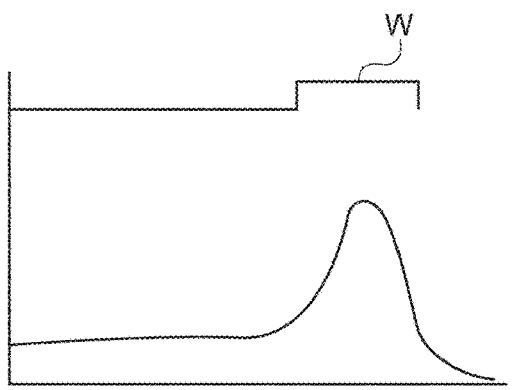

FIG. 1c illustrates the resulting broadened Bragg peak W.

Figure 2A:
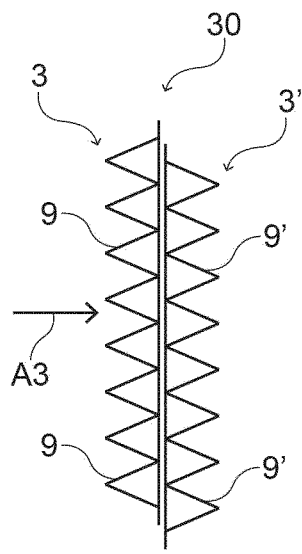
FIGS. 2a, 2b and 2c show a dynamic ripple filter unit according to an embodiment of the invention, in three different positions.
Figure 2B:
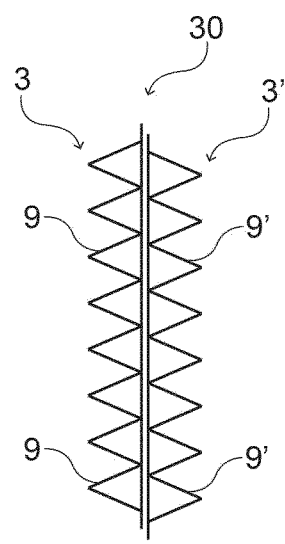
Figure 2C:
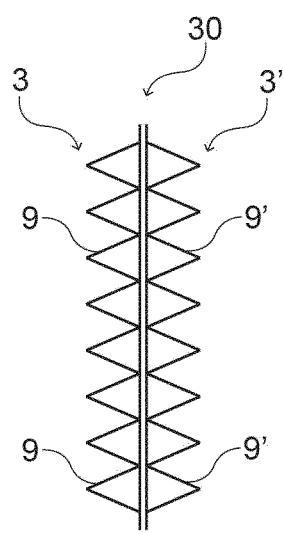

FIGS. 2a-2c illustrate a ripple filter unit 30 according to an embodiment of the invention comprising a first 3 and a second 3' ripple filter. As will be understood, the ripple filters 3, 3' can be designed in different ways as discussed in connection with FIG. 1b, but will comprise a pattern of ridges 9, 9' and valleys formed between the ridges. According to the invention, the ripple filters 3, 3' are placed in series so that a particle travelling towards a patient, in the direction shown by arrow A3, will pass through first the first ripple filter 3 and then the second ripple filter 3'. The two ripple filters are moved relative to each other to vary the filter characteristics of the ripple filter unit dynamically during treatment. The ripple filters 3, 3' are sometimes referred to in this document as simply filters 3, 3'.

In FIG. 2a, the filters 3, 3' are displaced relative to each other in such a way as to cause minimum modulation, by positioning the second filter 3' so that the peaks of its ridges coincide with the valleys of the first filter 3. In this case, a particle passing through the first filter 3 at a ridge will pass through the second filter 3' in a valley and vice versa, causing approximately the same energy loss across the whole filter.

FIG. 2b shows the same ripple filter unit 30 as in FIG. 2a but with a different displacement of the second filter 3' relative to the first filter 3. In the configuration shown in FIG. 2b, particles passing through the filter unit 30 in different positions will experience different degrees of attenuation, depending on the total width of the ridges of the filters 3, 3' in the position where it passes. This will cause different energy losses in the particles, which had the same initial energy, causing them to reach different depths in the patient, thereby effectively broadening the Bragg peak.

FIG. 2c shows a configuration of the ripple filter unit 30 in which the peaks of the two filters coincide so that a particle passing through the filter unit may pass through corresponding positions in both filters 3,3', that is, peaks in both filters, valleys in both filters or any position between the two extremes. This will cause the biggest difference between the energy losses of different particles in the energy layer and thus the greatest broadening of the Bragg peak.

Figure 2D:
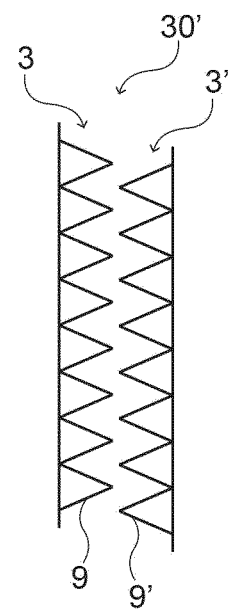
FIG. 2d shows a different configuration of a ripple filter unit according to an embodiment of the invention.

FIG. 2d shows an alternative configuration of a ripple filter unit 30', where the two filters 3, 3' are arranged with the ridges facing each other instead of the bases. The function of the ripple filter unit 30' is otherwise exactly like that of the ripple filter unit 30 of FIGS. 2a-2c.

As will be understood, the displacement between the first and the second ripple filter can be varied continuously between the extremes shown in FIG. 2a and FIG. 2c, respectively, thereby causing the desired modulation of the particles passing through the ripple filter unit.

The dimensions of the dynamic ripple filter unit may be adapted. A suitable total width has been found to be 0.1-1.5 cm. As for conventional ripple filters, the spatial separation between the ridges and the valleys should not be larger than the lateral width of the Bragg peak. This means that the spatial separation should typically be approximately 0.5-3 millimeters.

Figure 3A:
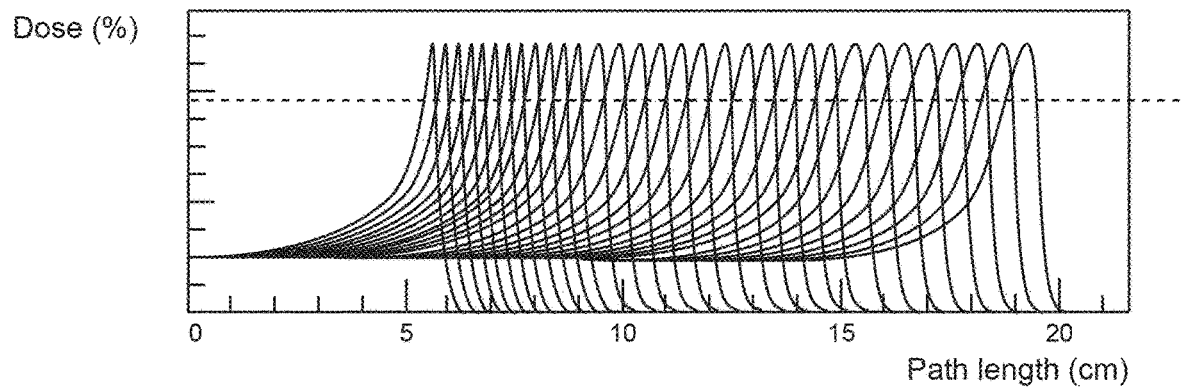
FIGS. 3a, 3b and 3c illustrate the resulting Bragg peaks and reduced number of energy layers when applying a dynamic ripple filter unit according to the invention.
Figure 3B:
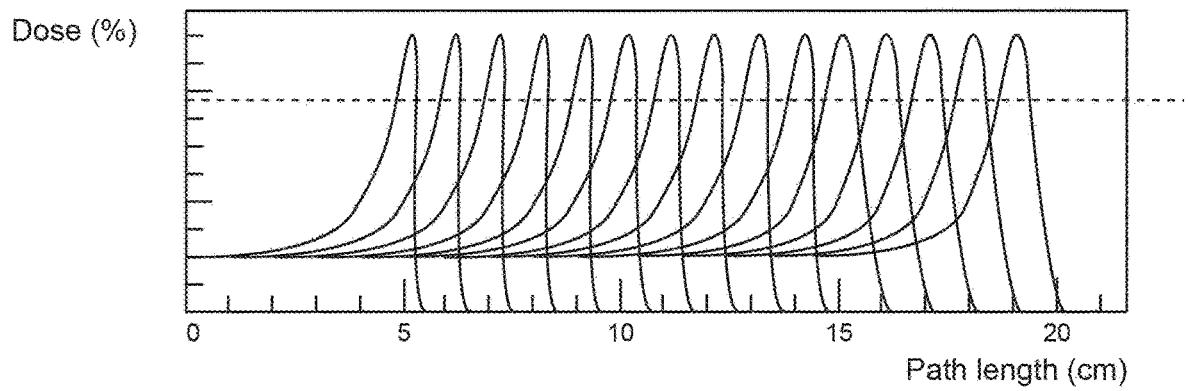
Figure 3C:
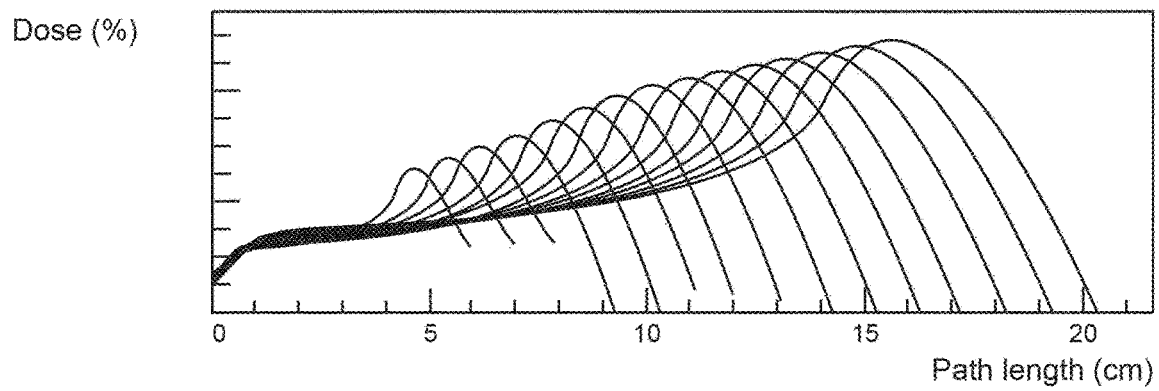

FIGS. 3a, 3b and 3c illustrate a resulting set of Bragg peaks when the number of energy layers are reduced by means of a dynamic ripple filter according to the invention. FIG. 3a shows the Bragg peaks of each energy layer with a prior art method, without any ripple filter. 80% of the maximum level is indicated by a horizontal dashed line. The Bragg peaks for the proximal peaks, to the left in the Figure, are significantly narrower than the Bragg peaks for the distal peaks, to the right in the Figure. Therefore, the lower energy layers, corresponding to the proximal Bragg peaks, must be closer together than the higher energy layers. A total of 32 energy layers are used and, as can be seen, the Bragg peaks overlap at or above the 80% level.

FIG. 3b shows the result of merely using fewer energy layers, keeping the same distance between all energy layers and without introducing any ripple filter. In FIG. 3b, 15 energy layers are used for the same area as in FIG. 3a, causing a greater distance between the Bragg peaks. Again, the 80% level is indicated by a dashed horizontal line. As can be seen, the overlap of the Bragg peaks is reduced so that between the Bragg peaks the deposited dose will be well below the 80% target level.

FIG. 3c shows the same number of energy layers as FIG. 3b but with a dynamic ripple filter according to the invention applied in the beam. For the distal peaks a small ripple is applied, whereas for the proximal peaks a greater ripple is applied, so that these peaks are broadened, which means that they will overlap at a higher level than in FIG. 3a. This also means that the proximal peaks will be significantly lowered because of the broadening, while the area under each curve is substantially unchanged. In this figure the neighboring curves attach at approximately their 80% level.

Figure 4:
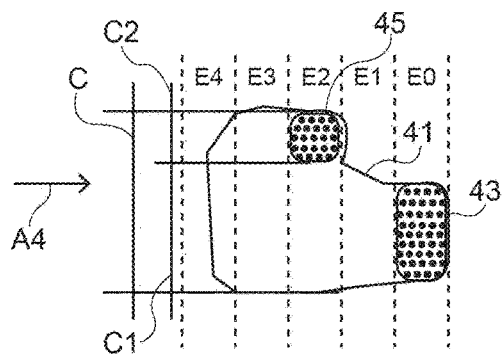
FIG. 4 illustrates a situation in which it may be desirable to use different settings for different spots within an energy layer.

So far, the invention has been discussed in the context of how to use different filter settings for different energy layers. FIG. 4 shows a situation in which it may be desirable to use different filter settings within an energy layer. In this case, five different energy layers E0-E4 are defined, to cover a simplified target 41 having a cross-section C at the incident angle of the beam. The target 41 has an irregular shape so that in one portion of the target, corresponding to a first sub-area C1 of the cross-section C, the highest energy layer E0 will reach the distal end of the target. In another portion of the target, corresponding to a second sub-area C2, it does not extend as far into the patient and the distal end will be at the third energy layer E2. This means that an area 43 of the target will want a sharp Bragg peak at the highest energy layer E0 but not necessarily on the third energy layer E2. Therefore, the ripple filter unit may be applied for particles in energy layer E2 aimed at the first sub-area C1 of the target. In the area 45, being the distal end of the target at the second sub-area C2, the Bragg peak should have a sharp distal edge and therefore the filters should be arranged as shown in FIG. 2a, to apply minimal modulation.

For example, in the example discussed in connection with FIG. 4, the ripple filter unit may be set differently for some spots in an energy layer than for other spots in that energy layer.

When optimizing a treatment plan, the optimization of the ripple filter settings for each energy layer may be taken into account, either as one single setting or as different settings within each energy layer. It should be noted that the word optimization is here used in the broadest possible sense. Hence, any way of determining a treatment plan is covered, including optimization using an objective function gradient based method or simply calculating a number of plans with different ripple filter settings and selecting the optimal plan. Plan optimality is determined as a trade-off between dosimetrical quality and other parameters such as delivery time. Overall flow charts of two possible methods are shown in FIGS. 5a and 5b.

Figure 5A:
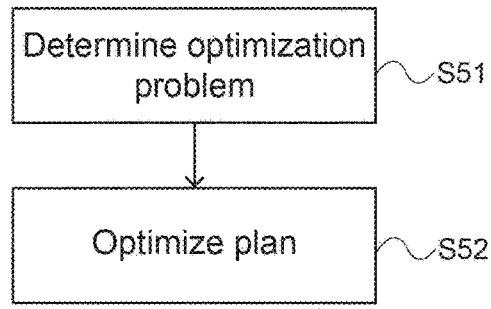
FIGS. 5a and 5b are flow charts of embodiments of the treatment planning method according to an aspect of the invention.

FIG. 5a illustrates a method in which the ripple filter settings are determined in a gradient-based optimization process. In step S51, therefore, the user defines an optimization problem including a penalty function that in one preferred embodiment strives to minimize the number of energy layers while maintaining overall plan quality. Instead of specifying the penalty function directly in terms of the number of energy layers, the user can specify a penalty function that strives to minimize delivery time while maintaining overall plan quality. This penalty function will also have the effect of reducing the number of energy layers. Alternatively, the user can choose to use multiple ripple filter settings per energy layers and a penalty function that maximizes plan quality independent from delivery time. Instead of using a penalty function, the user can specify a maximum number of allowed energy layers and/or the maximum delivery time and use this a constraint during the optimization. In step S52, the plan is optimized based on the optimization problem defined in step S51. This includes determining the ripple filter settings.

Figure 5B:
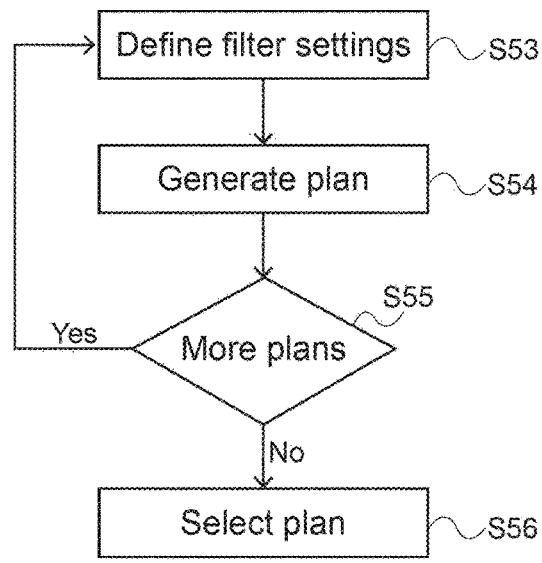

FIG. 5b illustrates an alternative plan optimization method, which includes generating a number of alternative plans and selecting one of them. In a first step S53, parameter settings are defined including ripple filter settings and in a second step S54, the corresponding plan is generated. In step S55 it is determined if the resulting plan is good enough or if another possible plan is to be generated. If yes, the procedure returns to step S53, in which new parameter settings are determined and a new plan generated. When it is determined in step S55 that no more possible plans should be generated, the procedure continues with step S56, in which one of the possible plans is selected, typically for delivery to a patient to be treated. An alternative method is to first produce plans for a range of range shifter settings and then evaluating all plans and selecting the best plan. As mentioned above, the selection is normally made based on delivery time and plan quality, for example, so that among the plans fulfilling the quality requirements, the plan having the shortest delivery time is selected.

The decision in step S55 may be made based on different criteria. For example, a preset number of plans may be generated and the plan having the lowest number of energy levels while still fulfilling the quality requirements may be selected. Alternatively, the steps S53 and S54 may be repeated until a plan involving a preset number of energy levels and fulfilling the quality requirements is obtained. In one implementation, the set of possible plans generated by iteration of steps S53 and S54 is generated to satisfy the quality requirements, and with a certain spacing of the Bragg peaks. A suitable start value might be based on the spacing between the two distal Bragg peaks. The Bragg peak widths could then be increased for lower energy levels, and the plans recalculated, that is, steps S53 and S54 repeated, until the plan quality was no longer satisfactory. The last calculated plan, that is, the plan with the widest spacing between the Bragg peaks that would still satisfy the quality requirements could be selected.

In the simplest case, the Bragg peaks may be set to have the same width for all energy layers. An overall better plan can be achieved if the width of the Bragg peaks is set to increase for decreasing energy layers thus reducing the distance between the Bragg peaks for lower energy layers. This will result in shorter delivery time, because the number of energy layers is reduced, but still with acceptable dosimetrical quality as the lower energy layers typically have lower weight in a plan.

When delivering the treatment plan to a patient, the software controlling the delivery will also control the settings of the ripple filter unit, so that the optimal smearing of the Bragg peak of each energy layer will be achieved. As discussed in connection with FIG. 4, the software may also be arranged to control the settings of the ripple filter unit differently for different spots within an energy layer.

Figure 6:
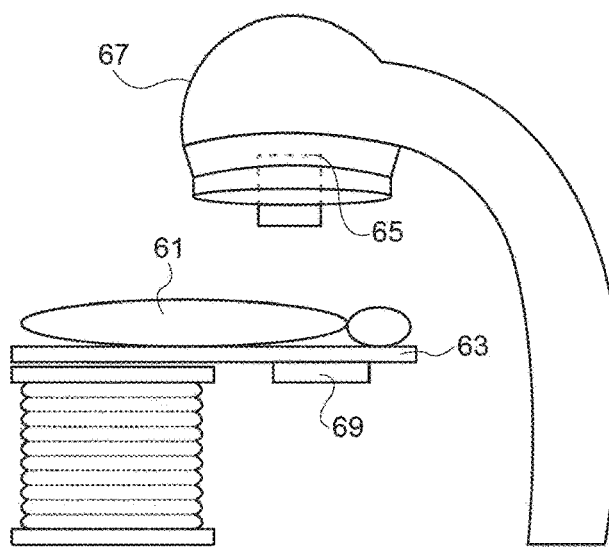
FIG. 6 shows schematically an apparatus for radiotherapy treatment planning and/or delivery.
Figure 6:
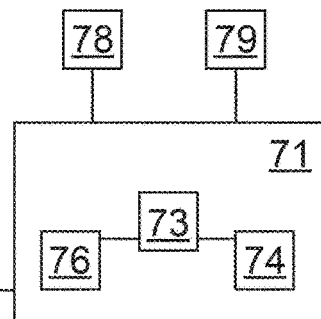

FIG. 6 is an overview of a system for radiotherapy treatment and/or treatment planning. As will be understood, such systems may be designed in any suitable way and the design shown in FIG. 6 is only an example. A patient 61 is positioned on a treatment couch 63. The system comprises a treatment unit having a radiation source 65 mounted in a gantry 67 for emitting radiation towards the patient positioned on the couch 63. Typically, the couch 63 and the gantry 67 are movable in several dimensions relative to each other, to provide radiation to the patient as flexibly and correctly as possible. These parts and their functions are well known to the skilled person. According to the invention, the gantry also comprises a ripple filter unit (not shown in FIG. 6) such as the one discussed above. The system also comprises a computer 71 which may be used for radiotherapy treatment planning and/or for controlling radiotherapy treatment. As will be understood, the computer 71 may be a separate unit not connected to the imaging unit.

The computer 71 comprises a processor 73, a data memory 74, and a program memory 76. Preferably, one or more user input means 78, 79 are also present, in the form of a keyboard, a mouse, a joystick, voice recognition means or any other available user input means. The user input means may also be arranged to receive data from an external memory unit.

The data memory 74 comprises clinical data and/or other information used to obtain a treatment plan, including a set of clinical goals to be used for planning. The data memory 74 also comprises device parameters specifying a penalty function set to minimize the number of energy layers. The data memory 74 also comprises one or more dose maps for one or more patients to be used in treatment planning according to embodiments of the invention. The program memory 76 holds a computer program, known per se, arranged for treatment plan optimization. The program memory 76 also holds a computer program arranged to make the computer perform the method steps discussed in connection with FIG. 5 and/or a computer program arranged to make the computer control the radiotherapy treatment of a patient, including the control of the ridge filter unit settings between energy layers, or within an energy layer.

As will be understood, the data memory 74 and the program memory 76 are shown and discussed only schematically. There may be several data memory units, each holding one or more different types of data, or one data memory holding all data in a suitably structured way, and the same holds for the program memories. One or more memories may also be stored on other computers. For example, the computer may only be arranged to perform one of the methods, there being another computer for performing the optimization.

The invention claimed is:

1. A ripple filter unit for expanding a particle energy distribution of a particle beam, comprising:

a first ripple filter and a second ripple filter, arranged in series, wherein the first ripple filter and the second ripple filter are movable relative to each other in such a way as to vary filter characteristics of the ripple filter unit dynamically by means of relative positions of the first ripple filter and the second ripple filter, wherein each of the first ripple filter and the second ripple filter comprises a pattern of ridges and valleys and the first ripple filter and the second ripple filter are moveable relative to each other in such a way as to displace the ridges of the first ripple filter and the second ripple filter relative to each other in a direction perpendicular to a direction of extension of the ridges, wherein each of the first ripple filter and the second ripple filter comprises a base on which the pattern of ridges and valleys are positioned, and wherein one of i) the pattern of ridges and valleys of each of the first ripple filter and the second ripple filter face each other, extend in a thickness direction, and extend laterally in a same direction, or ii) the bases of each of the first ripple filter and the second ripple filter face each other, extend in the thickness direction, and extend laterally in the same direction; and a controller for controlling the ripple filter unit by dynamically displacing the ridges of the first ripple filter and the second ripple filter relative to each other in a beam path during treatment.

2. The ripple filter unit according to claim 1, wherein either the first ripple filter or the second ripple filter is fixed and the ripple filter that is not fixed is arranged to be translated relative to the ripple filter that is fixed.

3. The ripple filter unit according to claim 1, wherein the first ripple filter is composed of uniform ridges positioned adjacent each other, and corners of a base of each ridge substantially touching adjacent ridges on both lateral sides of each ridge, except at edges of the first ripple filter, and wherein the second ripple filter is composed of uniform ridges positioned adjacent each other, and corners of a base of each ridge substantially touching adjacent ridges on both lateral sides of each ridge, except at edges of the second ripple filter.

4. A method of generating a radiotherapy treatment plan comprising the steps of:

a. determining device parameters including ripple filter settings for a ripple filter unit, the ripple filter unit including a first ripple filter and a second ripple filter, arranged in series, wherein the first ripple filter and the second ripple filter are movable relative to each other in such a way as to vary filter characteristics of the ripple filter unit dynamically by means of relative positions of the first ripple filter and the second ripple filter, wherein each of the first ripple filter and the second ripple filter comprises a pattern of ridges and valleys and the first ripple filter and the second ripple filter are moveable relative to each other in such a way as to displace the ridges of the first ripple filter and the second ripple filter relative to each other in a direction perpendicular to a direction of extension of the ridges, each of the first ripple filter and the second ripple filter comprises a base on which the pattern of ridges and valleys are positioned, one of i) the pattern of ridges and valleys of each of the first ripple filter and the second ripple filter face each other, extend in a thickness direction, and extend laterally in a same direction, or ii) the bases of each of the first ripple filter and the second ripple filter face each other, extend in the thickness direction, and extend laterally in the same direction, and the ripple filter settings including different filter settings for different energy layers or within an energy layer, each ripple filter settings including a dynamical and continuous displacement of the ridges of the first ripple filter and the ridges of the second ripple filter relative to each other in the direction perpendicular to the ridges, so as to achieve a defined Bragg peak modulation; and b. generating the radiotherapy treatment plan including said ripple filter settings.

5. The method according to claim 4, further comprising repeating steps a and b a number of times to generate a number of radiotherapy treatment plans and selecting one of the generated radiotherapy treatment plans and selecting one of the generated radiotherapy treatment plans based on a delivery time of each of the generated radiotherapy treatment plans.

6. The method according to claim 4, wherein the step of generating the radiotherapy treatment plan includes sequentially generating a first possible radiotherapy treatment plan using a first possible ripple filter setting and a second possible radiotherapy treatment plan using a second possible ripple filter setting and to select the first possible radiotherapy treatment plan or the second possible radiotherapy treatment plan based on a plan quality and a delivery time.

7. The method according to claim 4, wherein determining device parameters includes a step of defining an optimization problem including a component to determine the ripple filter settings in such a way as to reward a low number of energy layers.

8. A computer program product comprising computer readable code, stored on a non-transitory storage medium, which, when run in a processor will cause the processor to perform the method according to claim 4.

9. A radiotherapy treatment apparatus comprising a processor for controlling radiotherapy treatment and a program memory comprising the computer program product according to claim 8, arranged to be run in the processor to control the radiotherapy treatment apparatus.

10. A computer system comprising a processor, a data memory, and a program memory, wherein the program memory comprises the computer program product according to claim 8, wherein the computer program product is arranged to be run in the processor to control radiotherapy treatment planning.

11. A computer program product comprising computer readable code, stored on a non-transitory storage medium, which, when run in a processor will cause the processor to control a delivery of a pencil beam scan radiotherapy treatment to a patient and perform the method comprising:
controlling a ripple filter unit including a first ripple filter and a second ripple filter, arranged in series, wherein the first ripple filter and the second ripple filter are movable relative to each other in such a way as to vary filter characteristics of the ripple filter unit dynamically by means of relative positions of the first ripple filter and the second ripple filter, wherein each of the first ripple filter and the second ripple filter comprises a pattern of ridges and valleys and the first ripple filter and the second ripple filter are moveable relative to each other in such a way as to displace the ridges of the first ripple filter and the second ripple filter relative to each other in a direction perpendicular to a direction of extension of the ridges, wherein each of the first ripple filter and the second ripple filter comprises a base on which the pattern of ridges and valleys are positioned, and wherein one of i) the pattern of ridges and valleys of each of the first ripple filter and the second ripple filter face each other, extend in a thickness direction, and extend laterally in a same direction, or ii) the bases of each of the first ripple filter and the second ripple filter face each other, extend in the thickness direction, and extend laterally in the same direction, the controlling including modulating a width of Bragg peaks of spots in an energy layer or between individual spots in an energy layer by dynamically and continuously displacing ridges of the first ripple filter and ridges of the second ripple filter relative to each other.

12. The computer program product according to claim 11, wherein the computer readable code is arranged to control the ripple filter unit to modulate the width of the Bragg peaks per energy layer.

13. The computer program product according to claim 11, wherein the computer readable code is arranged to control the ripple filter unit to modulate the width of the Bragg peaks between different spots in an energy layer.

* * * * *